US012326444B2

(12) United States Patent
Kumta et al.

(10) Patent No.: US 12,326,444 B2
(45) Date of Patent: *Jun. 10, 2025

(54) DEVELOPMENT AND PARAMETER ASSESSMENT FOR VERTICALLY ALIGNED PLATINUM WIRE APTASENSOR ARRAYS FOR IMPEDIMETRIC DETECTION OF CARDIAC BIOMARKERS

(71) Applicant: UNIVERSITY OF PITTSBURGH—OF THE COMMONWEALTH SYSTEM OF HIGHER EDUCATION, Pittsburgh, PA (US)

(72) Inventors: Prashant N. Kumta, Pittsburgh, PA (US); Mitali Patil, Pittsburgh, PA (US)

(73) Assignee: UNIVERSITY OF PITTSBURGH-OF THE COMMONWEALTH SYSTEM OF HIGHER EDUCATION, Pittsburgh, PA (US)

( * ) Notice: Subject to any disclaimer, the term of this patent is extended or adjusted under 35 U.S.C. 154(b) by 798 days.

This patent is subject to a terminal disclaimer.

(21) Appl. No.: 17/471,788

(22) Filed: Sep. 10, 2021

(65) Prior Publication Data

US 2021/0405038 A1 Dec. 30, 2021

Related U.S. Application Data

(63) Continuation of application No. 15/765,306, filed as application No. PCT/US2016/055299 on Oct. 4, 2016, now Pat. No. 11,156,609.

(Continued)

(51) Int. Cl.
*G01N 33/543* (2006.01)
*G01N 27/327* (2006.01)
*G01N 33/68* (2006.01)

(52) U.S. Cl.
CPC ..... *G01N 33/5438* (2013.01); *G01N 33/6887* (2013.01); *G01N 27/327* (2013.01); *G01N 2800/32* (2013.01)

(58) Field of Classification Search
CPC .......... G01N 33/5438; G01N 33/6887; G01N 27/327; G01N 2800/32; G01N 33/558
See application file for complete search history.

(56) References Cited

U.S. PATENT DOCUMENTS

| 8,628,979 B2 | 1/2014 | Kas |
| 2005/0023155 A1 | 2/2005 | Sawyer et al. |

(Continued)

FOREIGN PATENT DOCUMENTS

| JP | 4949560 B2 | 6/2012 |
| JP | 2014530366 A | 11/2014 |

(Continued)

OTHER PUBLICATIONS

Extended European Search Report Issued in EP Application No. 20183546.9, Dated Aug. 28, 2020.

(Continued)

*Primary Examiner* — Dennis White
(74) *Attorney, Agent, or Firm* — Carol A. Marmo; Eckert Seamans Cherin & Mellott, LLC

(57) ABSTRACT

The invention relates to ex-situ biosensors that impedimetrically detect cardiac biomarkers of interest in a bodily fluid sample derived from a patient. The biosensors include a multi-array of vertically aligned platinum wires having immobilized thereon an aptamer that is selected to specifically and selectively bind to the cardiac markers of interest. The biosensors are contacted with a portion of the bodily fluid sample, and the aptamer binds to the cardiac markers of interest in the bodily fluid sample. As a result, an electrochemical impedance signal is generated and there- (Continued)

fore, a change in electrochemical impedance is indicative of the presence of the cardiac markers of interest in the bodily fluid sample. The biosensors are point-of-care, on-demand devices that can be used in a medical environment, as well as in domestic settings.

16 Claims, 3 Drawing Sheets

Related U.S. Application Data

(60) Provisional application No. 62/237,104, filed on Oct. 5, 2015.

(56) References Cited

U.S. PATENT DOCUMENTS

| | | |
|---|---|---|
| 2009/0326053 A1 | 12/2009 | Walsh et al. |
| 2013/0285680 A1 | 10/2013 | Sorgenfrei et al. |
| 2014/0255952 A1* | 9/2014 | Kumta .............. C12Q 1/42 |
| | | 435/7.4 |
| 2014/0272939 A1 | 9/2014 | Aghvanyan et al. |
| 2014/0342128 A1 | 11/2014 | Haynes et al. |
| 2015/0122669 A1 | 5/2015 | Davis et al. |
| 2015/0260717 A1 | 9/2015 | Kim et al. |

FOREIGN PATENT DOCUMENTS

| | | |
|---|---|---|
| JP | 2015516066 A | 6/2015 |
| JP | 2016520200 A | 7/2016 |
| WO | 2008020043 A1 | 2/2008 |
| WO | 2013057135 A1 | 4/2013 |

OTHER PUBLICATIONS

Martin-Fernandez, "Vertically Aligned Multi-Walled Carbon Nanotube Growth on Platinum Electrodes for Bio-Impedance Applications," Microelectronic Engineering 86 (2009), 806-808.

Kimmel et al., "Electrochemical Sensors and Biosensors," Analytical Chemistry (2011), 84:685-707.

Prabhulkar et al., Microbiosensor for Alzheimer's Disease Diagnostics: Detection of Amyloid Beta Biomarkers, Journal of Neurochemistry (2012), 122:374-381.

Patil et al., "Fabrication and Optimization of Vertically Aligned Platinum Wire Aptasensor Arrays (VAPPA) for Impedimetric Detection of Cardiac Biomarkers," Innovations in Biomedical Materials (pp. 13).

Tao et al., "The Preparation of Label-Free Electrochemical Immunsor Based on the Pt—Au Alloy Nanotube Array for Detection of Human Chronic Gonadotrophin," Clinica Chimica Acta (2010), 412(7):550-555.

Patil et al., "Platinum Aptasensor Wire Arrays for Cardiac Biomarker Detection," Materials Today Communications (2018), 15(1):55-60.

Extended European Search Report Issued in EP Application No. 16854163.9, Dated Mar. 26, 2019.

Martin-Fernandez, "Vertically Aligned Multi-Walled Carbon Nanotube Growth on Platinum Electrodes for Bio-Impedance Applications," Microelectronic Engineering 86 (2009), 406:1-14.

Garrett et al., Reproducible Fabrication of Robust, Renewable Vertically Aligned Multiwalled Carbon Nanotube/Epoxy Composite Electrodes, Analytical Chemistry (2011), 83:8347-8351.

* cited by examiner

DEVELOPMENT AND PARAMETER ASSESSMENT FOR VERTICALLY ALIGNED PLATINUM WIRE APTASENSOR ARRAYS FOR IMPEDIMETRIC DETECTION OF CARDIAC BIOMARKERS

CROSS-REFERENCE TO RELATED APPLICATION

This application is a continuation application of U.S. Patent Application having Ser. No. 15/765,306, filed on Apr. 2, 2018, which claims priority from U.S. National Stage Application under 35 U.S.C. § 371 of International Application No. PCT/US2016/055299, filed on Oct. 4, 2016, which claims priority under 35 U.S.C. § 119(e) from U.S. Provisional Patent Application No. 62/237,104, filed on Oct. 5, 2015, all of which are entitled "DEVELOPMENT AND PARAMETER ASSESSMENT FOR VERTICALLY ALIGNED PLATINUM WIRE APTASENSOR ARRAYS FOR IMPEDIMETRIC DETECTION OF CARDIAC BIOMARKERS," the contents of which are incorporated herein by reference.

FIELD OF THE INVENTION

The invention relates to multi-array, vertically aligned, platinum wire aptasensors for impedimetric detection of cardiac biomarkers in a biological sample, and diagnosis as well as prognosis of cardiovascular disease, including gauging the risk of cardiovascular disease in a patient. More particularly, the invention relates to an aptasensor device to provide on-demand, point-of-care screening, analysis and results.

BACKGROUND

Cardiovascular disease (CVD) is the leading cause of death in developed countries all around the world, including the United States. CVD encompasses several medical conditions of the heart and blood vessels, including coronary heart disease (CHD), which is the blockage of blood supply to the heart by the build-up of fatty deposits in the coronary arteries. Unattended, CVD can ultimately result in heart failure, stroke, and possible death. Statistics released by the American Heart Association indicate that CVD is the leading health problem and cause of death in the United States. Approximately 85.6 million people in the country suffer from some form of CVD, and one out of every three deaths results from heart disease, stroke and other CVDs, claiming more lives than all forms of cancer combined. In the United States alone, CVDs account for 31.9% of all deaths. According to statistics of the World Health Organization, CVD is the leading cause of death globally, and approximately 17.5 million people died from CVD in 2012. Nearly half the deaths resulting from CVD are the result of coronary heart disease alone. Direct and indirect costs of CVDs amount to more than $320.1 billion, constituting nearly 17% of national health expenditures. Unfortunately, the prevalence and costs of CVDs are projected to continue to increase over the years. It is estimated that the prevalence of CVD will rise from 37.8% to 40.5% and the costs will escalate from $350 billion to $818 billion by 2030.

Despite the considerable advances in the field of medicine, especially in CVD treatment, CVDs are and will continue to remain the leading cause of death in developed countries. This statistic is, at least in part, the result of a lack of standard method for diagnosis of CVD. The disease is clinically silent until serious complications arise. Diagnosis of CVD typically follows the onset of chest pains, electrocardiography results, and biochemical marker testing from blood samples. There are disadvantages associated with these diagnosis symptoms. Chest pains are not associated with CVDs alone; electrocardiography results are not always reliable; and processing blood sample paperwork and lab work can involve a period of several days, allowing critical time to lapse. Furthermore, imaging techniques such as magnetic resonance imaging (MRI), ultrafast computerized tomography (CT), and coronary and cerebrovascular angiography utilize expensive laboratory equipment and involve invasive procedures. Electrocardiography (ECG), based on electrical charges that occur during the heart cycle, is commonly used as a diagnostic tool for CVD due to its affordability and availability. However, ECGs produce a static picture that is not always indicative of the severity of the underlying CVD conditions and has only a 50% sensitivity. Thus, the lack of standard diagnostic methods and slow turnover for processing blood samples in hospital laboratories indicate the critical necessity of a point-of-care diagnostic biosensor for the rapid and sensitive detection of cardiac markers in blood.

Antibodies and enzymes are commonly utilized detection elements in biosensors due to their high affinity and specificity. However, there are disadvantages associated therewith—namely, antibodies and enzymes have relatively short shelf lives, are restricted by in vivo parameters, have batch-to-batch variation, and are sensitive to chemical or temperature changes. The use of synthetic aptamers (as compared to biological antibodies and enzymes) provide significant improvements for a biosensor. Aptamers are synthetic oligonucleotide sequences that are synthesized to bind to their target with high affinity and specificity, and therefore provide significant improvements for a biosensor. The synthetic process of producing aptamers ensures the following properties and characteristics: high stability in various environments, long shelf lives, and minimal batch-to-batch variation, while maintaining their affinity and specificity. The aptamer-based biosensor can provide a stable system that may be more easily translated to a medical device. Furthermore, the small size and lack of hydrophobic core in aptamers can prevent aggregation, which has been found to be problematic in antibodies.

Two particular biomarkers of interest in diagnosing the risk and prevalence of CVD are brain natriuretic peptide (BNP) and Troponin-T (TnT). BNP is a polypeptide secreted by the ventricles of the heart into the bloodstream upon excessive stretching of cardiomyocytes and is therefore an indicator of cardiac stress. TnT is a protein released into the bloodstream upon myocyte injury or death and is therefore an indicator of cardiac injury. Tailoring a biosensor to detect these two cardiac markers is of particular interest to the cardiovascular health community.

Synthesis of an impedimetric device requires a conductive material interface. There are advantages associated with the use and selection of platinum as the material interface, such as its chemically and electrochemically inert noble metal status, high conductivity, and biocompatibility. However, there are also disadvantages associated with platinum—most biosensor studies conducted on platinum interfaces still utilize antibodies and enzymes as detection elements, and often use platinum electrodes or nanoparticles in tandem with other material interfaces, such as, carbon nanotubes/nanocomposites, graphene, chitosan, silica, polymers, or gold. It is not known in the art to develop an aptamer-based biosensor on a platinum interface alone.

Various existing biosensor-based technologies are primarily based on fluorescent-immunoassays that require fluorescently-labeled antibodies and a bench-top analyzer for the fluorescent assay. Common immunoassays include membrane-based immunoassays such as lateral flow devices (LFD) and enzyme-linked immunosorbent assays (ELISAs). These tests are highly dependent on the use of fluorescently labeled antibodies and spectrophotometers for analysis of fluorescence levels. The assays are typically conducted in laboratories and require significant pre-analytical time and analytical time, which increases turn-around time. In addition, many of these devices require a greater volume of blood than a typical glucose detector.

In general, there is a lack of standard diagnostic methods, turnover of processing blood samples in hospitals and laboratories is frequently slow, and common diagnostic methods are expensive, time-consuming, invasive, requiring the patient to be tested in a medical facility and requiring the results to be obtained by skilled and trained personnel, which do not promote routine testing. Thus, there is a need for the development of improved impedimetric aptasensors capable of providing one or more of efficient, early, convenient (e.g., point-of-care, on-demand), inexpensive, rapid, minimally or non-invasive and accurate impedimetric detection and screening of multiple cardiac markers simultaneously and a diagnosis or prognosis of CVD risk in patients, in order to provide preventative medication and therapeutic treatment for favorable outcomes, which may be utilized outside the confines of a hospital or other medical facility, e.g., in a domestic setting, such as, a patient's home.

SUMMARY OF THE INVENTION

In one aspect, the invention provides a portable, ex-situ system to impedimetrically detect cardiac biomarkers of interest in a patient. The system includes a conductive material interface having a surface, and including an epoxy substrate and a multi-array of vertically aligned platinum wires cast in the epoxy substrate, a biological sensor agent applied to the surface of the conductive material interface. The biological sensor agent includes an immobilization agent, and at least one aptamer selected to interact with the immobilization agent and selected to bind with the cardiac biomarkers of interest. The system also includes a signaling agent consisting of an electrochemical impedance signal generated by binding of the aptamer with the cardiac biomarkers of interest; and a bodily fluid sample derived from the patient and in contact with the aptamer. A change in electrochemical impedance is indicative of a presence of the cardiac biomarkers of interest in the bodily fluid sample, and an absence of a change in electrochemical impedance is indicative of an absence of the cardiac biomarkers of interest in the bodily fluid sample.

An end of the platinum wires serves as the point of contact for the electrochemical impedance signals to be transduced, allowing for an interpretable reading of the output.

The bodily fluid sample can be a blood sample. The cardiac biomarkers can be selected from C-reactive protein, Creatinine Kinase, TroponinT, Myoglobin, IL-6, IL-18, Brain Natriuretic Peptide, and D-Dimer.

The aptamer can be conjugated with biotin. The immobilization agent can be selected from the group consisting of avidin, streptavidin, neutravidin and mixtures thereof The immobilization agent can be applied to a treating agent, and the treating agent can be applied to the surface of the conductive material interface including the multi-array of vertically aligned platinum wires.

The multi-array of vertically aligned platinum wires can be arranged on the surface of the substrate in a circular configuration.

The aptamer can be effective to impedimetrically detect simultaneously a plurality of cardiac biomarkers in the bodily fluid sample.

In another aspect, the invention includes a method of detecting cardiac biomarkers in a bodily fluid sample of a patient. The method includes obtaining the bodily fluid sample from the patient; forming a detection device including forming a conductive material interface having a surface, providing an epoxy substrate, obtaining a multi-array of vertically aligned platinum wires, and casting the multi-array of vertically aligned platinum wires in the epoxy substrate; polishing the surface of the conductive material interface; forming a biological sensor agent including applying an immobilization agent to the surface of the conductive material interface, selecting an aptamer to selectively bind with the cardiac biomarkers of interest, and interacting the aptamer with the immobilization agent; contacting the aptamer with the bodily fluid sample; generating an electrochemical impedance signal as a result of the aptamer binding with the cardiac biomarkers of interest; and assessing a presence or an absence of a change in electrochemical impedance. The presence of a change in electrochemical impedance is indicative of the presence of the cardiac biomarkers of interest in the bodily fluid sample, and the absence of a change in electrochemical impedance is indicative of the absence of the cardiac biomarkers of interest in the bodily fluid sample.

The electrochemical impedance signal can be transduced to an interpretable read-out value. The electrochemical impedance signal can be connected to a hand-held device that is effective to display the read-out value.

The detection device can be in the form of a test strip and the method, can include contacting the bodily fluid sample with the test strip; assessing a visual change to the test strip; correlating the visual change with a chart or key; and based on said correlating, determining if the visual change is indicative of the presence of a change in electrochemical impedance and the presence of the cardiac biomarkers in the bodily fluid sample. The visual change can also be a color change.

The polishing of the surface of the conductive material interface can be conducted to provide a surface roughness in a range from about 320 grit to about 2400 grit.

BRIEF DESCRIPTION OF THE DRAWINGS

A further understanding of the invention can be gained from the following description of the preferred embodiments when read in conjunction with the accompanying drawings in which.

DETAILED DESCRIPTION OF THE PREFERRED EMBODIMENTS

Figure 1:
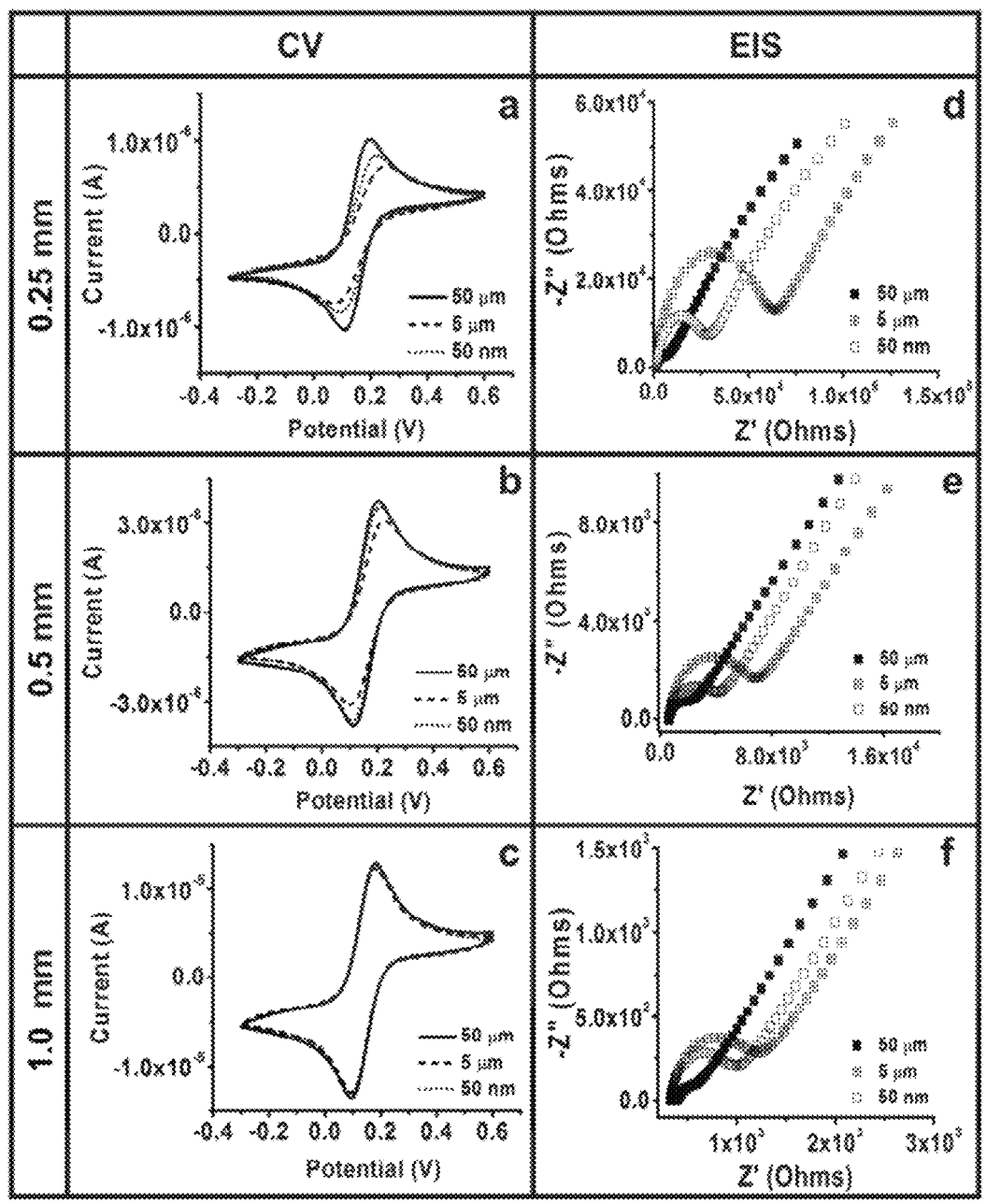
FIG. 1 shows cyclic voltammagrams and Nyquist interpretations of Electrochemical Impedance Spectroscopy (EIS) experiments conducted with Ag wire reference electrode and Pt wire counter electrode for platinum electrodes of different platinum wire diameters subjected to three polishing grits, in accordance with certain embodiments of the invention.

The invention relates to multi-array, impedimetric, vertically aligned platinum aptasensors for the impedimetric detection and screening of at least one cardiac biomarker, or multiple cardiac biomarkers simultaneously, present in bodily fluid, such as, blood, that signal the onset of, for example, artherosclerosis and/or inflammation of cardiac tissue and/or myocardial infarctions and/or cardiac dysfunctions. More particularly, the invention includes an electrochemical assay for electrochemically detecting cardiac biomarker concentrations that are present in a minimal amount of blood, e.g., a few drops of blood, by measuring, e.g., quantitatively, impedance changes that occur upon the binding of antigens to the aptasensors. Further, the invention includes methods of synthesizing the aptasensors that specifically and selectively bind to an intended target analyte, and employing the synthesized aptasensors for detecting and diagnosing myocyte stress and injury in a patient.

The aptasensors are in-vitro (ex-situ) devices that utilize the bodily fluid sample derived from the patient for impedimetric detection of the one or more cardiac biomarkers. The impedance changes are measured using electrochemical impedance spectroscopy (EIS), which is a highly sensitive, label-free technique that allows for changes in electrochemical impedance resulting from the binding of the aptamer to the antigen to be transduced into an interpretable read-out value. Thus, the aptasensor electrochemically detects cardiac biomarker concentrations present in the minimal amount of blood by measuring the ensuing impedance changes occurring upon antigens binding to the aptasensor.

As used in the specification and in the claims, the singular form of "a", "an", and "the" may include plural referents unless the context clearly dictates otherwise.

In general, according to the invention, aptamers are a form of biological detection (sensing) agent that are utilized to detect whether there exists certain analytes/biomarkers within a subject fluid sample. The term "aptamer" as used herein, refers to an oligonucleotide or oligonucleotide chain that has a specific and selective binding affinity for an intended target compound or molecule (e.g., analyte) of interest, and is capable of forming a complex with the intended target compound or molecule of interest. The complexation is target-specific in the sense that other materials which may accompany the target, do not complex to the aptamer. It is recognized that complexation and affinity are a matter of degree; however, in this context, "target-specific" means that the aptamer binds to the target with a much higher degree of affinity than it binds to contaminating materials. As used herein, the term "binding" refers to an interaction or complexation between the target compound or molecule of interest and the aptamer. Aptamers can be used in diagnosis by employing them in specific binding assays for the target compound or molecule of interest.

As used herein, "biomarkers" refer to naturally occurring or synthetic compounds, which are a marker of a disease state or of a normal or pathologic process that occurs in an organism. The term "analyte," as used herein, refers to any substance, including chemical and biological agents that can be measured in an analytical procedure. The term "bodily fluid", as used herein, refers to a mixture of molecules obtained from a patient. Bodily fluids include, but are not limited to, exhaled breath, whole blood, blood plasma, urine, semen, saliva, lymph fluid, meningeal fluid, amniotic fluid, glandular fluid, sputum, feces, sweat, mucous and cerebrospinal fluid. Bodily fluid also includes experimentally separated fractions of all of the preceding solutions or mixtures containing homogenized solid material, such as tissues and biopsy samples. According to the invention, biomarkers and/or analytes are detectable in bodily fluid, such as, but not limited to, a minute volume of blood.

An "array" is an intentionally created collection of molecules. The molecules in the array can be identical or different from each other.

The systems (e.g., biosensors) and methods of the invention can include at least one biological sensor agent and at least one signaling agent wherein the biological sensor agent(s) and signaling agent(s) together provide a means for detecting, signaling, and/or quantifying target compounds of interest in bodily fluids, such as, blood. The biological sensor agent is selected for its ability to specifically and selectively interact with and bind to (only) the target analyte/biomarker molecules. In accordance with the invention, the biological sensor agent is attached to the surface of a conductive material interface. The biological sensor agent can be introduced by functionalization of the surface of a conductive material interface. The biological sensor agent can be directly attached to the conductive material interface or indirectly attached by employing linker molecules, such as, but not limited to, proteins. The conductive material is a multi-array of vertically aligned platinum wires cast in an epoxy substrate. The biological sensor agent is in the form of an aptamer. For example, an aptamer-linked protein can be immobilized on a surface of the conductive material interface. The aptamer can be conjugated to a signaling agent, e.g., the electrochemical impedance signal. The signaling agent is detectable under preselected conditions, e.g., after aptamer binding to the analyte/biomarker of interest. In accordance with the invention, signaling is related to a change in impedance, upon binding of the aptamer with the analyte/biomarker of interest. An end of the platinum wires provides a point of contact for an electrochemical impedance signal to be transduced to an interpretable read-out value.

In certain embodiments, the invention utilizes platinum wire as a conductive material interface and platform for a biosensing surface. The immobilized biological sensor is applied to the platform. The immobilized biological sensor includes the aptamer, e.g., biotinylated aptamer, and the immobilization agent. Furthermore, the signaling agent includes the electrochemical impedance signal. The aptasensor is tailored to detect various cardiac markers predictive of cardiovascular disease (CVD) in bodily fluids, primarily, but not limited to, blood, to determine the risk state of a patient for CVD. The sample of bodily fluid can be a minute volume, such as, for example, a few drops (e.g., about 1-5 drops) of blood, and the determination can be obtained in a relatively short period of time, such as, for example, about several minutes to five minutes. The cardiac markers can include C-reactive protein, Creatinine Kinase, TroponinT, Myoglobin, IL-6, IL-18, Brain natriuretic Peptide, and D-Dimer. Brain Natriuretic peptide (BNP) is an indicator of myocyte stress and Troponin-T (TnT) is an indicator of myocyte injury. In contrast, known systems for detecting CVD include magnetic resonance imaging (MRI), computerized tomography (CT), electrocardiography (ECG) and invasive techniques, such as, coronary and cerebrovascular angiography. For systems focused on blood work, enzyme-linked immunosorbent assays (ELISA) and lateral flow devices (LFD) can be employed. These analyses and devices for detection involve expensive equipment, highly-skilled and trained personnel for proper analysis, associated risks and a significant amount of time for processing, which includes analytical time, e.g., the duration of the assay, and pre-analytical time, involving paperwork, drawing samples, labeling samples and enormous preparation time. The multi-array aptasensors in accordance with the invention provide portable, point-of-care, on-demand devices that can be utilized in the absence of expensive equipment and highly trained professionals to assess levels of cardiac markers in the blood at the patient's bedside, for example, within a short period of time, such as, several minutes. Since the use of these aptasensors do not require much skill or training, they represent a simple and facile mode of detection.

Further, known impedimetric devices utilize antibodies and enzymes as detection elements, and platinum is used in tandem with other material interfaces such as carbon nanotubes/nanocomposites, graphene, chitosan, silica, polymers, or gold. In contrast, the multi-array aptasensors in accordance with the invention utilize platinum alone as the material interface.

Synthesis of the multi-array aptasensors, in accordance with the invention, includes the use of appropriate linkers and proteins to immobilize cardiac marker-specific aptamers to the surface of the platinum wires. The platinum wire arrays, e.g., vertically aligned, are embedded in an epoxy mold, e.g., in a circular fashion or pattern, and the surface of the epoxy mold is polished, e.g., to approximately 50 nm, for surface exposure. The surface then can be treated with a thiol-based compound, such as, an aminothiol, including but not limited to, cysteamine and/or glutaraldehyde. An immobilization agent, such as, avidin, is adsorbed thereon. One or more aptamers is conjugated with biotin. The biotinylated aptamers for the above-described cardiac markers interact with the immobilization agent to develop the biosensing surface. Application of the treating agent and the immobilization agent, and interaction of the biotinylated aptamers can be carried out in a sequential manner, to develop the biosensing surface. As previously described, aptamers are similar to antibodies in that aptamers are oligonucleotide sequences that are highly specific for their designated antigen. However, unlike antibodies, aptamers can undergo denaturation and renaturation. The aptasensors can therefore be regenerated in the presence of certain solvents, thus providing a reusable and regenerative sensor for potentially continuous use rather than one-time detection (as in commercially known glucose sensors). Thus, aptamers are more robust with a longer shelf-life and more importantly, allowing for aptasensors to be reusable rather than only a one-time, single-use assay.

An electrochemical sensor can be used to measure a change in output of a sensing element caused by chemical interaction of a target marker on a sensing element. In accordance with the invention, electrochemical impedance spectroscopy (EIS) is the technique, e.g., sensor agent, utilized to characterize the surface of an aptasensor at various stages of development. EIS is a highly sensitive and label-free technique that allows for changes in electrochemical impedance resulting from the binding of the aptamer to the antigen. The electrochemical impedance can be transduced to a read-out value. Thus, the aptasensor is capable of electrochemically detecting cardiac biomarker concentrations that are present in a minimal amount of blood by measuring the impedance changes that occur upon the binding of antigens to the aptasensor. The impedimetric detection of the cardiac biomarker can be performed within minutes, and the aptasensor can be reused for this purpose multiple times.

In accordance with the invention, vertically aligned modified platinum wire-based aptasensors are provided for the impedimetric detection of cardiac markers. The aptasensors are synthesized by casting upright platinum wires in epoxy. The wires can be cast in various configurations and patterns. In certain embodiments, the wires are cast in a circular pattern. The diameter of the wires may vary and can range from about 0.25 mm to about 1.0 mm. In certain embodiments, the diameter is about 0.25 mm or about 0.5 mm or about 1.0 mm.

One end of the wire is cast in the epoxy and the opposite end has an immobilized aptamer attached thereto. Thus, the wires are utilized for functionalization and establishing electrical connection.

The resulting platinum electrodes are polished using polishing media, such as, but not limited to, silicon carbide (SiC), to various different grits and functionalized to bind the cardiac biomarker-specific aptamers to the surface. The surface roughness can vary and, for example, the polishing grit size, can range from about 320 grit (e.g., about 50 µm) to about 2400 grit (e.g., about 50 nm). In certain embodiments, the grit size is about 320 grit or about 1200 grit (e.g., about 5 µm) or about 2400 grit. It is contemplated and understood that the impedimetric devices can be tested against various clinically relevant concentrations of cardiac biomarker to determine the ideal wire diameter and polishing grit.

In certain embodiments of the invention, the aptasensors utilize 0.5 mm-diameter wires polished to about 1200 grit (e.g., 5 µm) size.

Electrochemical impedance spectroscopy (EIS) can be employed as a mode of impedimetric detection for the one or more cardiac biomarkers.

Impedimetric biosensors provide one or more of the following features and advantages as compared with known biosensors of CVD: highly sensitive, low cost, allow for rapid analysis and miniaturization, and label-free, thus significantly reducing the complexity of biosensor development.

There are various conventional mechanisms for functionalizing, e.g., attaching an aptamer thereto, the platinum wires including, but not limited to, adsorbing a binding material thereon. The binding material is selected based on its capability to bind particular aptamer. Non-limiting examples of suitable binder materials include avidin, streptavidin, and neutravidin. In certain embodiments, neutravidin is preferred. Further, the aptamer for binding to the avidin is selected based on its capability to interact with the target biomarker. Non-limiting examples of suitable aptamer include biotinylated aptamer selected specifically for cardiac biomarkers, such as, but not limited to, those described herein, for example, BNP and TnT. Thus, the avidin is immobilized on the surface of the platinum wires and the biotinylated aptamer attaches to the avidin.

The process of biotinylation generally includes covalently attaching biotin to a protein, nuclei acid or other molecule. Biotin is known to bind to avidin with high affinity. The aptamer can be biotinylated chemically or enzymatically using conventional processes and apparatus.

In certain embodiments, the multi-array of platinum wires is embedded in an epoxy substrate, the surface of the epoxy substrate is polished and the wires on the surface of the epoxy substrate are treated with avidin followed by biotinylated aptamer. The biotinylated aptamer can include biotinylated proteins. In certain embodiments, the biotinylated aptamer is selected based on its ability to interact with cardiac biomarkers. Thus, BNP and TnT aptamer may be selected to interact with BNP and TnT biomarker, respectively. These cardiac biomarkers are released into bodily fluids, e.g., blood, for example, as a result of myocyte stretching or injury or death.

The biosensors developed in accordance with the invention may function as ex-situ biosensors. A portable (e.g., point-of-care, on-demand) device, such as, a handheld device, may be developed. There are various mechanisms that are known in the art to produce a handheld device that may be employed with the biosensors, and are suitable for use with the biosensors of the invention. In certain embodiments, the electrochemical impedance signal is transduced to a read-out value, and the read-out value is displayed on a handheld device. The handheld device can be an electronic device. Alternatively, the handheld device can include, for example, a test strip similar to conventional glucose sensors which are known in the art. There is typically a corresponding standard chart or key used to interpret the results displayed on the test strip. In these embodiments, the test strip is contacted with a patient bodily fluid sample, such as by applying the sample, e.g., a few drops, to the test strip or by dipping/immersing the test strip into the bodily fluid sample. The test strip is then visually observed or inspected to determine whether there is a visible change, such as a change in color, based on its contact with the sample. The mere presence of a visual change, such as color change, is indicative of a change of electrochemical impedance, e.g., binding of the aptamer in the test strip with the cardiac biomarkers in the bodily fluid sample, and therefore, the presence in the sample of the cardiac biomarkers of interest. Further, the corresponding key or chart can include varying degrees or intensity of change. The degree or intensity of visual change on the test strip is correlated to a particular quantitative amount of the electrochemical change and corresponding level of cardiac biomarkers of interest in the sample. Similarly, the absence of a visual change on the test strip is indicative of the absence of the cardiac biomarkers of interest in the patient bodily fluid sample.

For example, in accordance with certain embodiments of the invention, a bodily fluid sample, such as blood, is obtained or removed from a patient. Further, the sample can be obtained or removed by the patient. At least a portion of the sample is deposited on the test strip and within a time period, e.g., seconds or a few minutes, a change in color of at least a portion of the test strip is visually observed based on the cardiac biomarkers in the sample interacting with the test strip, e.g., biosensor. The particular color and/or the intensity of the color change is compared and matched with a key to determine the level of the cardiac biomarker, e.g., BNP and/or TnT, in the sample. Based on the visible change of the biosensor, the presence or absence or particular concentration of the cardiac biomarker is determined efficiently and accurately. The response time may be in minutes or even seconds, and the results can be obtained by the patient in a domestic setting, without the need for medical personnel, laboratory equipment and a medical facility.

Therefore, impedimetric biosensors in accordance with the invention are ideal portable, e.g., point-of-care, on-demand, diagnostics that can be used, for example, at bedside, in ambulances, or even during clinical visits as a useful screening device for the detection of cardiac biomarkers and therefore, the diagnosis of CVD.

Further, in accordance with the invention, impedimetric biosensors exhibiting the following attributes are provided: (i) re-usable aptamer-based electrochemical assay; (ii) multiple cardiac biomarker detection in a single setting; and (iii) amenable to hand-held model translation.

Point-of-care handheld aptasensors in accordance with the invention allow patients to frequently detect and measure their cardiac biomarkers and therefore, assess their individual CVD risk and to monitor how different lifestyle changes can reduce this risk. In addition, the aptasensors are inexpensive, e.g., comparable in price to blood-based glucose biosensors that are currently commercially available. Further, existing insurance codes for glucose biosensors and cardiac biomarker testing could be readily applied to aptasensors for full or partial reimbursement of the cost. Thus, patients can affordably, routinely and rapidly detect and measure their cardiac biomarkers.

In an emergency room setting, significant minimization of turn-around time may be realized, resulting in more efficient allocation of resources and providing more effective care for patients. For example, decreasing the time of diagnosis can reduce the time required to make an admission decision and therefore, ensure administration of rapid care to the patient. In addition, decreasing the time of diagnosis may also ensure that patients suffering from less severe conditions are not allocated more expensive, redundant resources.

In certain embodiments, the aptasensors can be tailored with a wireless chip to allow for wireless transmission of biomarker levels to a patient's electronic health records. Thus, reducing the amount of paperwork necessary and allowing the physician to directly view trends in the levels of biomarkers and detecting early a precarious patient CVD situation. In an overall health-care system setting, the aptamers may eventually allow for the replacement of antibodies with aptamers for immunoassays.

It should be understood that the embodiments described herein and the examples provided below are for illustrative purposes only and that various modifications or changes in light thereof will be suggested to persons skilled in the art and are to be included within the spirit and purview of this application.

EXAMPLES

In accordance with the invention, impedimetric vertically-aligned platinum wire-based aptasensors for the detection of cardiac markers BNP and TnT were developed and parameter assessment (specifically, diameter of wire and surface polishing) was conducted. Upright platinum wires of varying diameters were cast in epoxy such that one end was utilized for functionalization and the other end was used to establish electrical connection. The resulting platinum electrodes were accordingly polished to various different grits, functionalized to bind the BNP and TnT-specific aptamers to the surface, and tested against various clinically relevant concentrations of BNP and TnT to determine the ideal parameters (wire diameter and polishing grit) for biosensor and medical device development.

1. Example

Three surface polishes (50 µm, 5 µm, 50 nm) and three platinum wire diameters (0.25 mm, 0.5 mm, and 1.0 mm) were characterized, functionalized, and then tested against clinically relevant concentrations of BNP and TnT to assess which parameter was optimum for detecting BNP and TnT without losing precision or sensitivity. The ideal parameter for the vertically-aligned platinum wire array was found to be 0.5 mm diameter wire polished to 5 µm. Therefore, the feasibility of the developed platinum aptasensor and the ideal parameters required for the aptasensor were demonstrated.

2. Experimental Procedure

2.1. Reagents

Potassium ferrocyanide and potassium ferricyanide were purchased from Fisher Scientific; cysteamine was purchased from Acros Organics; glutaraldehyde was purchased from Sigma-Aldrich; avidin was purchased from Thermo-Fisher Scientific; brain natriuretic peptide (BNP) and TroponinT (TnT) biotinylated aptamers were purchased from OTC Biotech; brain natriuretic peptide antigen was purchased from ABDSerotec; and TroponinT antigen was purchased from LeeBio. All the aqueous solutions were either prepared in Phosphate-Buffered Saline (PBS) purchased from Lonza or in Millipore de-ionized water (18 M$\Omega$cm$^{-1}$).

2.2. Electrode Preparation

Vertically aligned platinum wires (0.25 mm dia, 0.5 mm dia, and 1.0 mm dia, 99.9% metals basis, Alfa Aesar) were cast in a non-conducting epoxy resin disk (Buehler) in a circular pattern and polished to 50 µm on 320 grit, 5 µm on 1200, and 50 nm on 2400 grit silicon carbide paper (Allied High Tech Products, Inc.). The resulting disk was sonicated in de-ionized water followed by 95% EtOH, for five minutes each prior to electrochemical characterization and functionalization.

2.3. Electrochemical Characterization

All electrochemical characterization was carried out using the Gamry series G Potentiostat in an electrolyte solution of 5 mM potassium ferro/ferricyanide redox couple in 10 mM PBS (Fe(CN)$_6$$^{3-/4-}$) with silver wire as the reference electrode and platinum wire as the counter electrode. For electrode characterization, both cyclic voltammetry (CV) and electrochemical impedance spectroscopy (EIS) experiments were conducted, and for functionalization and antigen binding assessments, the EIS experiments were conducted after each step. CV experiments were carried out across a potential range of −0.4V to 0.6V at a scan rate of 100 mV/s, and EIS experiments were carried out across a frequency range of 300,000 Hz-0.01 Hz with an AC amplitude voltage of 10 mV rms. Resultant Nyquist plots were analyzed using Z-view (Scribner Associates, Inc.) to determine the charge-transfer resistance values.

2.4. Electrode Functionalization

The platinum electrodes were treated with 10 mg/mL cysteamine prepared in de-ionized water for 1 hour at room temperature, followed by 25% glutaraldehyde in water for 1 hour at room temperature for thiolation and carboxylation of the surface. The surface was then treated with 1 mg/mL neutravidin prepared in 10 mM PBS for 2 hours at room temperature, followed by incubation with biotinylated aptamer (for 2 hours at room temperature). The electrodes were then stored in PBS at 4° C. until time of use.

2.5. Antigen Testing

Four concentrations for both BNP and TnT were prepared, each within the clinical range for low to high risk for cardiovascular disease. BNP-aptamer biosensors were successively treated with 0.2 ng/mL, 0.6 ng/mL, 1.0 ng/mL, and 2.0 ng/mL BNP, and TnT-aptamer biosensors were successively treated with 0.005 ng/mL, 0.01 ng/mL, 0.02 ng/mL, and 0.04 ng/mL TnT, to develop a calibration curve for future biosensor testing. EIS measurements were taken after each antigen incubation for the development of the calibration curves.

3. Results & Discussion

3.1 Characterization of Electrode Parameters

Three disks of vertically aligned platinum wire electrodes were prepared—0.25 mm diameter, 0.5 mm diameter, and 1.0 mm diameter platinum wire electrodes—and each disk was polished to grits of 50 µm, 5 µm, 50 nm. Thus, a total of nine parameters were characterized, functionalized, and tested for antigen detection. Electrochemical characterization of the bare platinum electrodes for the nine possible parameters (as shown in FIG. 1) demonstrated that an increase in diameter led to an increase in current passage through the electrode (as shown in FIG. 1, views a-c) and accordingly, a decrease in the charge-transfer resistance (as shown in FIG. 1, views d-f). As the diameter of the electrode increased, the peak currents had a tendency to cluster together, demonstrating that the polishing had less of an impact on the current passage. However, the 50 µm polished electrode consistently had the highest peak currents, while the 5 µm consistently had the lowest peak currents. The 50 µm polished electrodes had the lowest charge-transfer resistance and the 5 µm polished electrodes had the highest charge-transfer resistance. While the range of charge-transfer resistances across polishing decreased, there were substantial differences between polishing, especially between 50 µm and 5 µm. This established EIS as a highly sensitive technique as compared to known techniques, such as, cyclic voltammetry.

3.2 Biosensor Functionalization and Antigen Detection

Figure 2:
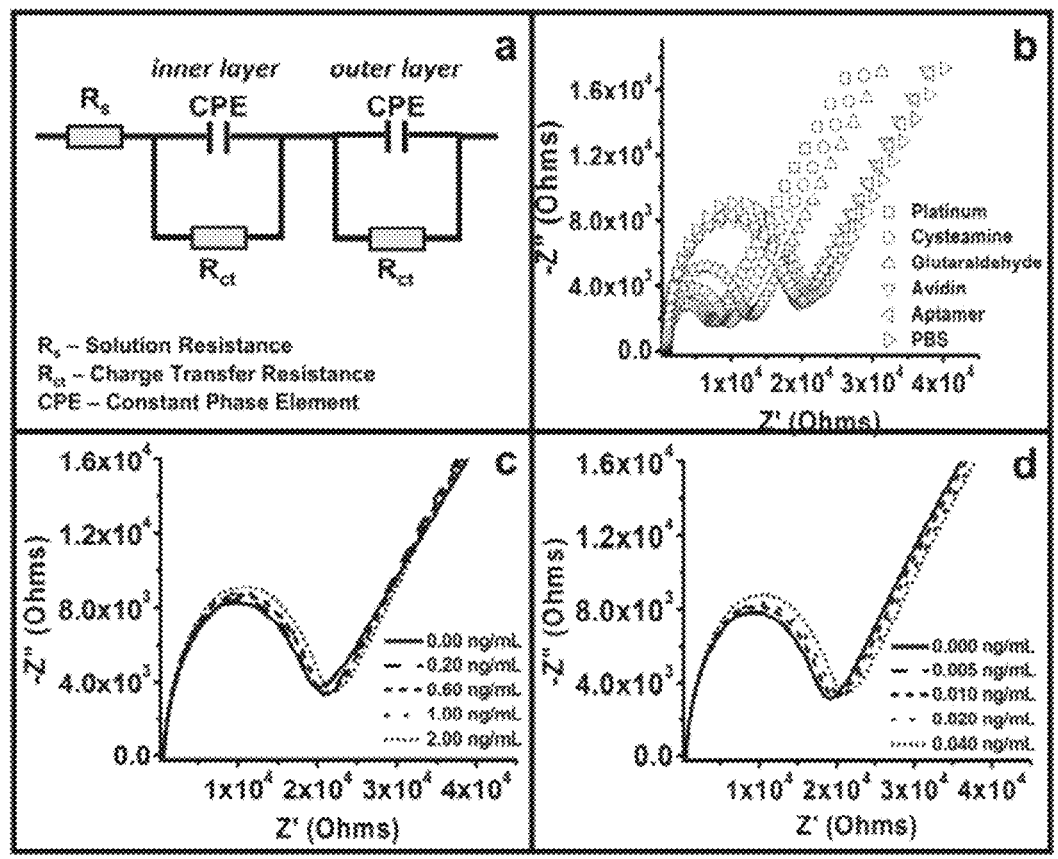
FIG. 2 shows Nyquist interpretations of EIS experiments conducted in 5 mM $(Fe(CN)_6)^{3-/4-}$) in 10 mM PBS, with 5 µm polished 0.5 mm diameter platinum working electrodes, Ag wire reference electrode, and Pt wire counter electrode, in accordance with certain embodiments of the invention.

All charge-transfer resistances obtained from EIS characterization at any stage of the experiment fit the equivalent circuit shown in FIG. 2a, which depicted a solution resistance (due to the ferro/ferricyanide electrolyte) in series with two constant phase element (CPE) components, with each CPE component in parallel to a resistance component. The CPE components were the result of an electrochemical double layer, which was indicative of exposure of the electrode to the electrolyte, thus creating two parallel layers of charge—the first layer being surface charge resulting from the chemical interactions on the surface, and the second layer being ions attracted to but loosely associated with the surface charge (known as a diffuse layer). Each CPE-$R_{ct}$ circuit was marked as inner layer or outer layer, with the inner layer being the semicircular portion of the Nyquist plot, and the outer layer being the second portion of the Nyquist plot, which would represent a second semicircle with further extrapolation of the plot. The inner layer represented the chemical interaction of interest, while the outer layer represented the possible interaction of ions with other charged layers of the electrode/biosensor. FIG. 2b demonstrates the multiple chemical interactions required to bind the sensor element (aptamers) to the platinum electrode surface. Cysteamine, glutaraldehyde, avidin, and aptamer were added in succession of one another, followed by storage in PBS (which served as the buffer fluid and as the 0.00 ng/mL baseline for the antigen detection experiments). As each component was added to the biosensing surface, the charge transfer increased (FIG. 2b), with Avidin binding demonstrating the largest change in charge-transfer resistance from the previous layer due to its large size compared to cysteamine, glutaraldehyde, and aptamers. Once the biosensors were prepared, the biosensors were tested for antigen detection for four clinically relevant concentrations of BNP (FIG. 2c) and TnT (FIG. 2d) respectively. As the antigen concentration increased, the charge transfer resistance increased, thus indicating that as more antigen bound to the aptamer on the surface of the biosensor, the impedance increased, thus allowing the concentration to be electrochemically quantified as a charge-transfer resistance value.

Figure 3:
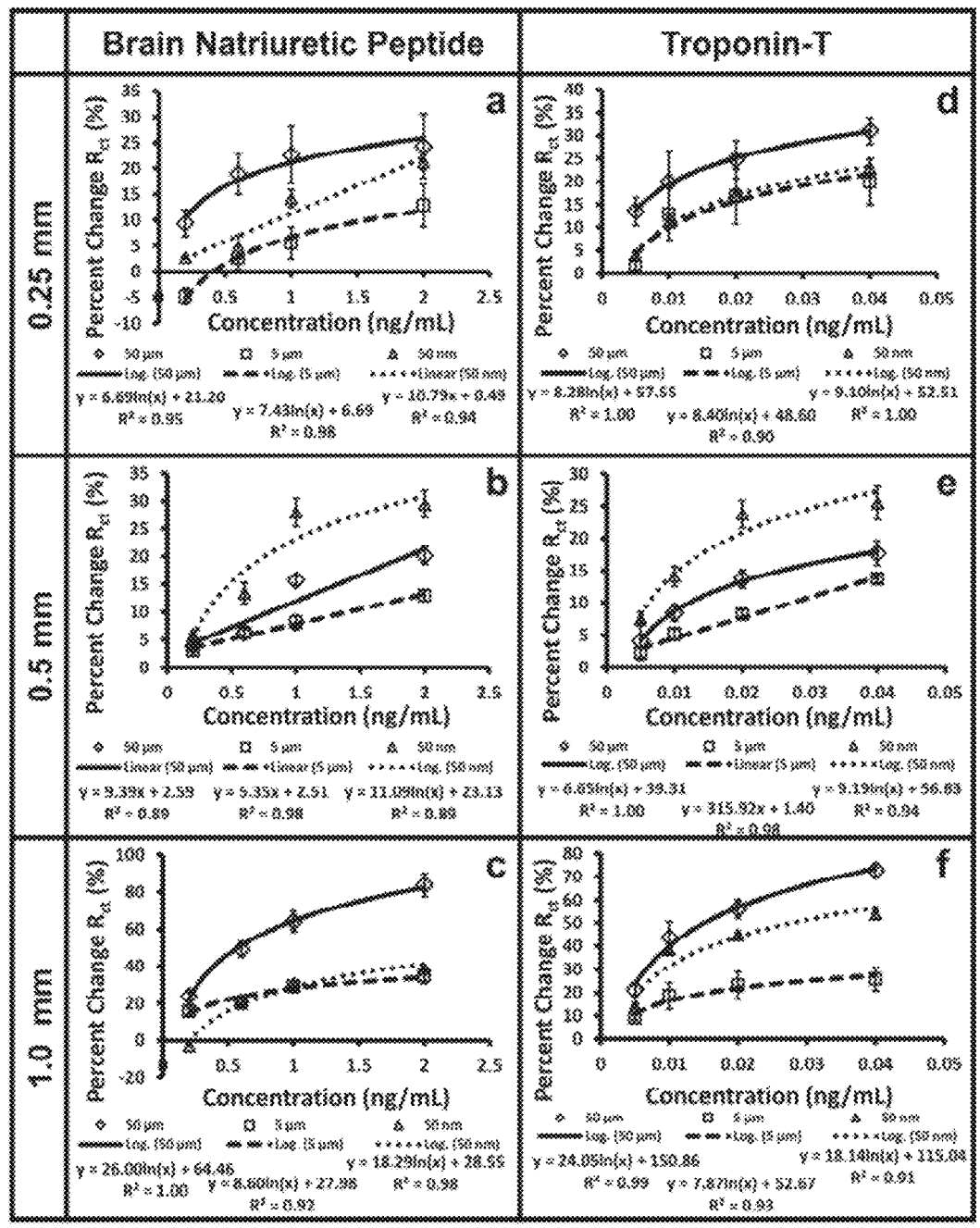
FIG. 3 shows calibration curves depicting average percent change in charge-transfer resistance as a function of concentration and standard error for platinum-based aptasensors of three polishing grits at different platinum wire diameters, in accordance with certain embodiments of the invention.

3.3 Linearity and Reproducibility of Calibration Curves for Biosensor Parameters Once all nine parameters were electrochemically tested for both BNP and TnT antigen detection through EIS, the percent change between each antigen charge-transfer resistance value and the baseline charge-transfer resistance value was calculated and plotted against the concentration to determine the calibration curve for each parameter for both BNP (FIG. 3a-c) and TnT (FIG. 3d-f). Saturation in these clinically relevant levels was indicative of the biosensor's lack of sensitivity at these crucial concentrations. However, linearity was indicative of the biosensor's success to detect within the crucial concentration range and possibly beyond that range as well. Standard error (n=3) was calculated for each concentration at each parameter, with a smaller standard error being indicative of precision and reproducibility while larger standard errors were indicative of inconsistency across the electrodes. Therefore, the parameter that demonstrated excellent linearity and precision for both BNP and TnT would be the ideal parameter. At the 0.25 mm diameter, all but one parameter (50 nm) saturates for BNP (FIG. 3a), and all parameters saturate for TnT (FIG. 3d). At the 0.5 mm diameter, both 50 μm and 5 μm for BNP demonstrated linearity, but the correlation between concentration and percent change in charge-transfer resistance was smaller for 50 μm ($R^2$=0.89) than for 5 μm ($R^2$=0.98). All parameters save for 5 μm saturated in TnT (FIG. 3e), and the 5 μm calibration curve had an excellent correlation ($R^2$=0.98). At the 1.0 mm diameter, all parameters saturated for both BNP (FIG. 3c) and TnT (FIG. 3f). Therefore, the ideal parameter was determined to be 0.5 mm wire polished to 5 μm. This parameter may have been ideal due to the fact that rougher surfaces (50 μm) tend to be better for protein attachment than smoother surfaces (50 nm) due to greater surface area, but rougher surfaces can also induce greater protein denaturation (Rechendorff 2006, Dolatshahi-Pirouz 2008). Thus, a surface that is between these two spectrum would be ideal (5 μm). The same compromise could be extended to wire diameters, where the smaller diameter (0.25 mm) had reduced area for binding, while the larger diameter (1.0 mm) had larger area for binding, but also a higher probability of expressing inconsistencies or defects on the surface (Nishida 1992, Van Noort 2013). Thus, the middle diameter (0.5 mm) was ideal.

4. Conclusions

In summary, a simplistic upright platinum wire-based multi-array impedimetric biosensor was effective to detect markers indicative of myocyte stress (BNP) and myocyte injury (TnT). This simplistic design required no labeling, was cost-effective, and upon subsequently being scaled down and miniaturized, requires no expensive and esoteric instrumentation. The ideal parameter of 0.5 mm platinum wire polished to 5 μm was determined for achieving effective and consistent detection.

The invention claimed is:

1. A portable, handheld device to detect a cardiac biomarker of interest in a patient, comprising:
    at least one aptasensor, comprising:
        vertically aligned platinum wires cast in an epoxy substrate;
        a biological sensor agent comprising an immobilization agent, applied to the vertically aligned platinum wires; and
        one or more aptamers selected to interact with the immobilization agent and bind with the cardiac biomarker of interest;
    a test strip substrate comprising the at least one aptasensor;
    a bodily fluid sample derived from the patient in contact with the test strip substrate; and
    a displayed result comprising a visual change present on a surface of the test strip substrate or a visual change absent on a surface of the test strip substrate,
        wherein the device is configured such that in its use, presence of the visual change on the surface of the test strip substrate is indicative of a presence of the cardiac biomarker of interest in the bodily fluid sample and binding with the one or more aptamers, and absence of the visual change on the surface of the test strip substrate is indicative of an absence of the cardiac biomarker of interest in the bodily fluid sample and binding with the one or more aptamers; and
    a pre-calibrated chart that shows one or more visual changes for correlation with the displayed result.

2. The device of claim 1, wherein the visual change is a color change on at least a portion of the surface of the test strip surface.

3. The device of claim 1, wherein the visual change is a color intensity change on at least a portion of the surface of the test strip surface.

4. The device of claim 1, wherein the bodily fluid sample is a blood sample.

5. The device of claim 1, wherein the cardiac biomarker is selected from C-reactive protein, Creatinine Kinase, TroponinT, Myoglobin, IL-6, IL-18, Brain Natriuretic Peptide, D-dimer, and combinations thereof.

6. The device of claim 1, wherein the at least one aptasensor is effective to detect simultaneously more than one cardiac biomarker of interest present in the bodily fluid sample.

7. The device of claim 1, wherein the one or more aptamers is/are conjugated with biotin.

8. The device of claim 1, wherein the pre-calibrated chart correlates the displayed result to a quantitative level of the cardiac biomarker of interest present in the bodily fluid sample.

9. The device of claim 1, wherein the pre-calibrated chart comprises a varying degree or intensity of visual change such that the degree or intensity of visual change on the test strip is correlated to a quantitative level of the cardiac biomarker of interest present in the bodily fluid sample.

10. The device of claim 6, wherein the pre-calibrated chart correlates the displayed results to a quantitative level of the more than one cardiac biomarker of interest present in the bodily fluid sample.

11. The device of claim 6, wherein the pre-calibrated chart comprises a varying degree or intensity of visual change such that the degree or intensity of visual change on the test strip is correlated to a quantitative level of the more than one cardiac biomarker of interest present in the bodily fluid sample.

12. A method of detecting a cardiac biomarker in a bodily fluid sample of a patient, comprising:
    forming a portable, handheld device, comprising:
        forming at least one aptasensor, comprising:
            casting vertically aligned platinum wires in an epoxy substrate;

applying a biological sensor agent comprising an immobilization agent to the vertically aligned platinum wires; and selecting one or more aptamers to interact with the immobilization agent and bind with the cardiac biomarker of interest;

forming a test strip substrate comprising the at least one aptasensor;

contacting the test strip substrate with a bodily fluid sample derived from the patient;

generating a displayed result comprising a visual change present on a surface of the test strip substrate or a visual change absent on a surface of the test strip substrate, wherein the device is configured such that in its use, presence of the visual change on the surface of the test strip substrate is indicative of a presence of the cardiac biomarker of interest in the bodily fluid sample and binding with the one or more aptamers, and absence of the visual change on the surface of the test strip substrate is indicative of an absence of the cardiac biomarker of interest in the bodily fluid sample and binding with the one or more aptamers;

forming a pre-calibrated chart that shows one or more visual changes for correlation with the displayed result; and assessing the displayed result by comparing and correlating the displayed result with the pre-calibrated chart.

13. The method of claim 12, wherein the assessing step further comprises determining a quantitative level of the cardiac biomarker present in the bodily fluid sample by correlating the pre-calibrated chart with the displayed result.

14. The method of claim 12, wherein the one or more aptamers is effective to selectively bind with more than one cardiac biomarker and the test strip substrate is effective to indicate simultaneously the more than one cardiac biomarker present in the bodily fluid sample.

15. The method of claim 14, wherein the assessing step further comprises determining a quantitative level of the more than one cardiac biomarker present in the bodily fluid sample by correlating the pre-calibrated chart with the displayed result.

16. The method of claim 12, wherein the generating step comprises the visual change in the form of a color change on at least a portion of the surface of the test strip substrate.

* * * * *